United States Patent …

(12) United States Patent
Hörnig

(10) Patent No.: US 7,463,719 B2
(45) Date of Patent: Dec. 9, 2008

(54) METHOD FOR ACQUIRING A SERIES OF X-RAY IMAGES

(75) Inventor: Mathias Hörnig, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 96 days.

(21) Appl. No.: 11/715,537

(22) Filed: Mar. 8, 2007

(65) Prior Publication Data
US 2007/0211860 A1 Sep. 13, 2007

(30) Foreign Application Priority Data
Mar. 10, 2006 (DE) .................... 10 2006 011 243

(51) Int. Cl.
*H05G 1/30* (2006.01)

(52) U.S. Cl. .......................................... 378/116; 378/24

(58) Field of Classification Search ............ 378/21–27, 378/207, 114–116
See application file for complete search history.

(56) References Cited

U.S. PATENT DOCUMENTS

2005/0105679 A1   5/2005   Wu et al.
2008/0101537 A1*  5/2008   Sendai .................... 378/23

FOREIGN PATENT DOCUMENTS

DE            199 14 217 A    10/2000

* cited by examiner

*Primary Examiner*—Hoon Song

(57) ABSTRACT

During tomosynthesis a plurality of x-ray images is acquired. The angular position of the x-ray tube is changed from x-ray image to x-ray image. Absorption in the imaged object (patient) and also in the patient table changes as a function of the angle. To compensate for this, backlight is applied while the x-ray images are being acquired. The intensity of the back light is selected as a function of the angle of the x-ray tube to the normal of the flat x-ray detector. Backlight can also be directed during reading, with only the areas already read in each instance being irradiated.

17 Claims, 2 Drawing Sheets

(Stand der Technik)

(Stand der Technik)

(Stand der Technik)

(Stand der Technik)

METHOD FOR ACQUIRING A SERIES OF X-RAY IMAGES

CROSS REFERENCE TO RELATED APPLICATIONS

This application claims priority of German application No. 10 2006 011 243.1 filed Mar. 10, 2006, which is incorporated by reference herein in its entirety.

FIELD OF THE INVENTION

The invention relates to a method for acquiring a series of x-ray images, in particular in the nature of the tomosynthesis method.

BACKGROUND OF THE INVENTION

With a tomosynthesis method a conventional x-ray tube and a flat x-ray detector are used. The x-ray tube is moved successively into a plurality of angular positions. An angle can be defined as the angle between a connecting line from the x-ray tube to a (selected, typically central) point on the flat x-ray detector and the surface normal of the flat x-ray detector (which would not be a flat x-ray detector without the definition of a surface with a surface with a surface normal). At least one x-ray image is acquired in each angular position by switching the flat x-ray detector to sensitive over the period of a time window and emitting x-ray radiation by way of the x-ray tube within the time window. With a tomosynthesis method the additional features must be present that the individual images are each acquired with a different focus of the x-ray radiation and then combined to form an overall image. These features are however of no further relevance in the context of the method claimed here.

The most important thing here is that different x-ray images are acquired based on different angular positions of the x-ray tube.

Depending on the angle setting, the x-ray radiation travels through different distances at the patient and at the patient bed. The absorption in the patient and patient table therefore varies with the angular position. Therefore the power arriving at the flat x-ray detector is variable. It can happen that the flat x-ray detector is not operated in an optimum mode, for example because the image signals are too weak. Flat x-ray detectors have different working areas, which can be roughly divided into a working area, wherein the received dose is too low, with the result that non-linear effects occur, a working area, wherein the received dose is a mean dose, with the result that the required linearity of the received signals is achieved with the received x-ray dose, and a working area, wherein the x-ray dose is too high, with the result that non-linear effects occur here too.

It is desirable for the flat x-ray detector to operate essentially in the middle working area. It might be an obvious solution to vary the power of the x-ray tube, to obtain correspondingly variable x-ray doses at the flat x-ray detector. However this would mean that the individual images acquired in the context of the tomosynthesis would no longer be comparable. As mentioned above, these are to be combined to form an overall image.

SUMMARY OF THE INVENTION

The object of the invention is to ensure an optimum operating mode of the flat x-ray detector during tomosynthesis or the method of the type mentioned above.

The object is achieved by a method according to the claims.

According to the invention a flat x-ray detector is used, which has a backlight functionality. The backlight functionality per se is known in the prior art. A plurality of light-emitting electrodes is attached to the rear of the detector. The light emitted by the light-emitting electrodes also strikes the detector elements. Since the detectors convert the x-ray radiation to light by way of scintillators, said light being detected by photodetectors, and since the photodetectors can also detect the backlight, the backlight acts as an additional x-ray dose. With the inventive method backlight is applied within the time window. The backlight thus increases the x-ray dose in a virtual manner, as a result of which the flat x-ray detector can switch from a working area of possibly too low a dose to the appropriate working area, wherein the x-ray signals can be processed optimally. To resolve the above-mentioned problem, an additional feature is provided with the invention, in that the backlight intensity can be set differently for different angular positions of the x-ray tube. Setting can take place on the basis of empirical values, which are stored in a table for example. It is also possible to predetermine a formula as a function of the angle, with information about the angle being available in any case in conventional x-ray C-arm systems.

By varying the backlight intensity it is possible to compensate for at least the basic tendency of the effect of the different distances. Precise regulation cannot be effected such that the receive signal level is essentially identical in the flat x-ray detector. It is however also possible to approximate to this state, such that the effect of the different distances is at least alleviated by the backlight.

In a preferred embodiment the backlight is applied in each instance over the entire period of the time window. This ensures a uniform impact of the backlight.

In a further preferred embodiment the backlight intensity is a function of the dose of x-ray radiation emitted by the x-ray tube. The x-ray dose then represents a second parameter for setting the backlight intensity. The dependency can be captured in a table, such that activation of the backlight can take place automatically in a corresponding manner by means of a computer system. Since the x-ray dose is generally a function of the voltage at the x-ray tube, the x-ray tube voltage can also be selected as a parameter.

It is essentially also true here that the backlight intensity should be selected in such a manner that the flat x-ray detector switches to a receive signal level area (through the interaction of x-ray radiation on the one hand and backlight on the other hand), wherein receive signals change in a linear manner with the received x-ray dose. There are no absolute proportionalities here, simply linear dependencies of the respective changes.

The backlight, once introduced, can also be used expediently to compensate for a further effect: during tomosynthesis the different images are generally acquired in very fast time succession during movement of the x-ray tube. Detector artifacts occur in this process. If the time sequence between two images is too short, residual image structures from the previous image appear in the next image (what is known as the memory effect).

It is known that the backlight can also be advantageous here. Backlight raises electrodes activated by the x-ray radiation in the previous image in the photodetector into the conduction band. The electrodes then no longer contribute to disruptive conduction currents, which play a role in the production of artifacts.

In order not to eliminate the previous image, if it has not yet been read, the backlight is only applied after reading. The invention intervenes here in an optimized manner: generally a flat x-ray detector is read area by area (in each instance after the end of an acquisition time window). With the preferred embodiment of the invention the backlight is applied specifically to the already read areas in each instance while reading is carried out or continued. It is not possible to eliminate the artifacts more quickly than with this preferred embodiment.

BRIEF DESCRIPTION OF THE DRAWINGS

A preferred embodiment of the invention is described below with reference to the drawing, in which.

DETAILED DESCRIPTION OF THE INVENTION

Figure 1A:
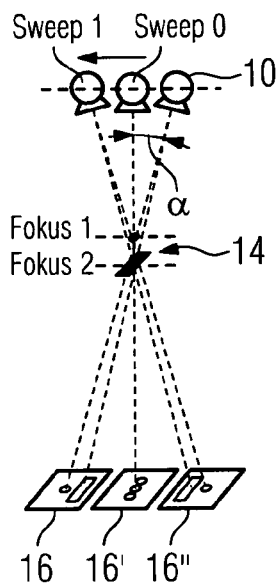
FIG. 1A shows a schematic diagram of the acquisition situation during tomosynthesis.
Figure 1B:
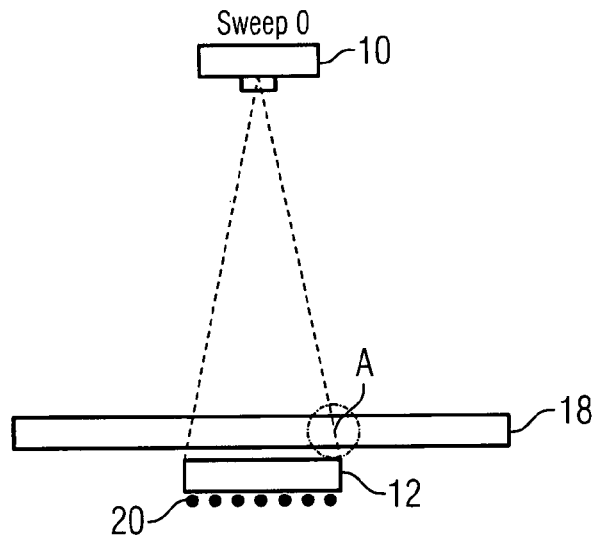
FIG. 1B shows the acquisition situation in a first angular position.
Figure 1C:
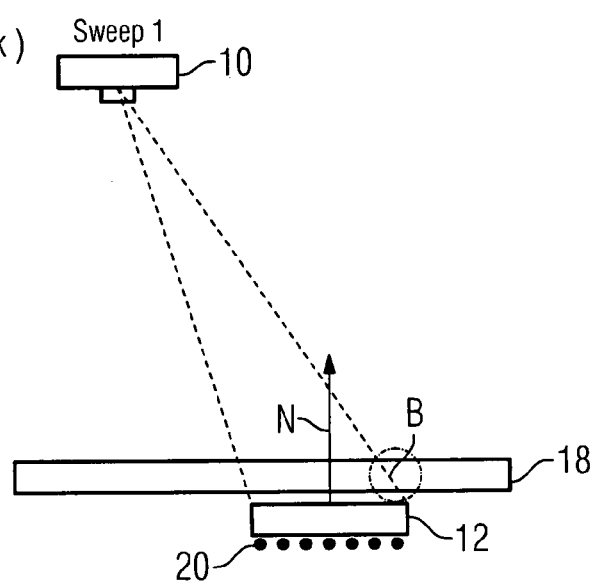
FIG. 1C shows the acquisition situation in a second angular position, with FIG. 1D showing the different distances through the patient table in the two angular positions according to FIG. 1B and FIG. 1C.

FIG. 1A to FIG. 1C show schematic diagrams of an x-ray tube 10, which can assume different positions. The x-ray tube 10 can be moved into different angular positions in relation to a flat x-ray detector 12 (FIG. 1B/1C). During tomosynthesis images are acquired for different angular positions of the x-ray tube 10. The focus of the x-ray radiation is varied in this process. This means that different areas within the patient 14 are imaged (symbolized by the circle to be imaged and the rectangle to be imaged). In the three angular positions shown in FIG. 1A three images 16, 16' and 16" are obtained. The sharpness of the imaged circle on the one hand varies from image 16 to image 16", as does the sharpness of the imaged rectangle. In reality different focal planes within the patient 14 are shown first sharply and then not sharply. Tomosynthesis involves a particularly sophisticated superimposition of the individual images 16, 16' and 16" to form an overall three-dimensional data record. Skilled selection of the change of focus allows the extraction of slice images, in which required objects are shown particularly sharply, while the surrounding area is shown with a particular lack of sharpness.

We will not look any further at tomosynthesis. Tomosynthesis per se is also known under this term in the prior art.

Figure 1D:
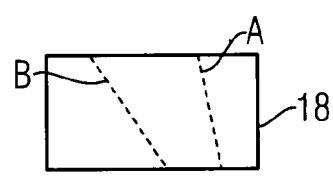

It is essentially of lesser importance here that the x-ray focus is set differently from angular position to angular position. More important is a difference in the x-ray dose striking the flat x-ray detector 12. In a first angular position (sweep 0 in FIG. 1B) the x-ray radiation in the patient table 18 follows the path A. Where there is a larger angle in relation to the surface normal N of the flat x-ray detector 12, as shown in FIG. 1C, the x-ray radiation follows the path B in the patient table 18. The difference between path A and path B is shown in FIG. 1D. When the x-ray radiation strikes the patient table 18 at a steeper angle, the path is shorter: path A is clearly smaller than path B.

The same applies to the distances the x-ray radiation passes through in a patient lying on the bed 18 (not shown).

One problem with tomosynthesis is therefore that the x-ray dose striking the flat x-ray detector 12 varies as the angle α (FIG. 1A) changes.

This means that the respective flat x-ray detector 12 does not operate in the optimum working area. For example in the case of FIG. 1C the absorption over the distance B can be so great that too much x-ray radiation is absorbed and the dose striking the individual detector elements is too small in each instance. In other words the receive signal level is not sufficiently high. This means that a receive signal level area of the flat x-ray detector 12 is used, which is not optimized and wherein non-linear effects can occur.

The invention resolves this problem in that backlight is applied by a backlight functionality during acquisition of the x-ray image. The backlight functionality is shown symbolically by the points 20 in FIG. 1B and FIG. 1C, which symbolize a matrix of LEDs.

Figure 2:
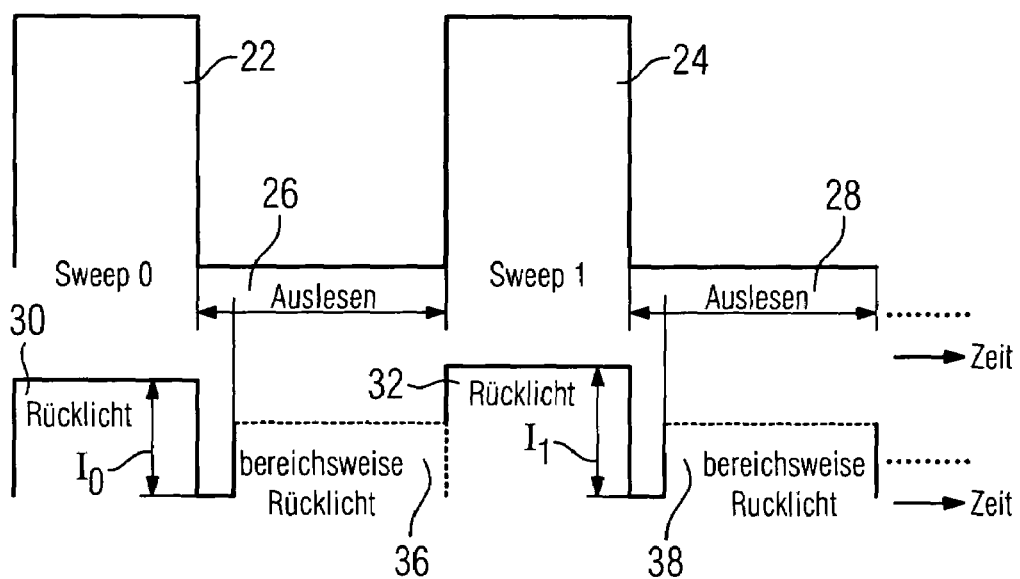
FIG. 2 shows a schematic diagram of the temporal link between the application of backlight and the operation of the x-ray system.

The temporal scan for this process is shown in FIG. 2. The upper part of FIG. 2 shows the steps of the x-ray system, while the lower part of FIG. 2 shows the temporally assigned backlight output.

In FIG. 2 the rectangular boxes 22 and 24 represent the acquisition of x-ray images in the position according to FIG. 1B (sweep 0) or in the position according to FIG. 1C (sweep 1).

The rectangles 22 and 24 respectively represent the time window, during which the flat x-ray detector 12 is switched to sensitive. The x-ray radiation is generally emitted by way of the x-ray tube 10 during this very time window. The time windows 22 and 24 follow in very quick succession, in other words the change in angular position takes place on the time plane of the acquisition of individual images. (In reality the different between two adjacent positions should not be quite a large as shown in FIG. 1B and FIG. 1C. Instead a plurality of images is acquired between two such extreme positions.)

Provision is made for reading the flat x-ray detector during a time window 26 or 28 between the time windows 22, 24.

As shown in the lower part of FIG. 2, backlight is applied precisely over the period of the entire time window 22 (rectangle 30). Backlight is also applied over the period of the time window 24 (rectangle 32). The intensity of the backlight is hereby symbolized by the height of the respective rectangle 30 or 32. The rectangle 32 is shown as higher than the rectangle 30. This corresponds to a higher backlight intensity, because the increased absorption of the x-ray radiation due to the longer distance B (see FIG. 1D) compared with distance A in the case of sweep 1 has to be compensated for compared with sweep 0. One important aspect is therefore the provision of a higher intensity for a larger angle.

Figure 3:
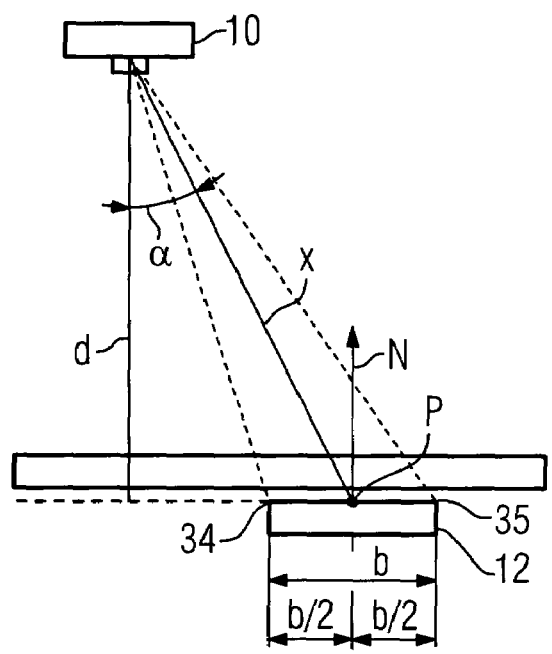
FIG. 3 shows the variables used to calculate an angle-dependent backlight application.

The intensity $I_1$ can be calculated from the intensity $I_0$. Let $I_1 = I_0 \cdot V$ apply, where V is a gain factor and $I_0$ relates to the situation where radiation is perpendicular to the flat x-ray detector 12 (FIG. 1B). V can then be calculated as follows: the angle α is defined as the angle between the surface normal N of the flat x-ray detector 12 (see FIG. 3) and the connecting line from the x-ray tube 10 to a point on the flat x-ray detector 12. A point in the center of the flat x-ray detector is selected here: if the edges 34 and 35 of the flat x-ray detector 12 are at a distance b from each other, the point P is at a distance b/2 from both edges 34 and 35.

The distance from the x-ray tube 10 to the point P on the flat x-ray detector 12 is x. The distance in a direction parallel to the surface normal N is d. The ratio of x to d corresponds precisely to the lengthening of the distance covered by the x-ray radiation when it follows the path corresponding to the connecting line x compared with the perpendicular strike. This ratio can therefore serve as a gain factor for the backlight intensity, when a corresponding x-ray radiation absorption has to be compensated for as here. The following therefore applies:

$$V = \frac{x}{d} = \frac{1}{\cos\alpha} \cdot I_1 = \frac{I_0}{\cos\alpha}$$

therefore results.

$I_0$ is defined for where $\alpha=0$ (FIG. 1B) and can assume an empirical or any other value. It is important that the backlight intensity increases in inverse proportion to the cosine of the angle $\alpha$.

A further aspect relates to backlight emission during the read steps 26 and 28. The backlight can for example cause the detector elements to be reset, thereby ensuring the elimination of residual image structures. It is naturally not recommended that the backlight should be applied to the areas of the x-ray image, which have not yet been read. Reading therefore takes place area by area according to steps 26 and 28. As symbolized by the rectangles 36 and 38, the backlight is then applied specifically to those very areas of the flat x-ray detector 12, which have already been read. (The individual LEDs hereby operate at constant intensity, which can be rather lower than $I_0$. The increase in the number of LEDs is not shown in FIG. 2.)

The invention therefore uses the backlight for two purposes: on the one hand to switch the flat x-ray detector to an optimum working area, such that the angular position no longer has a disruptive effect on imaging and angular influences are also compensated for. Secondly the invention uses the backlight to eliminate residual image structures.

The invention claimed is:

1. A method for acquiring a series of x-ray images by an x-ray device comprising an x-ray tube and a flat x-ray detector in a medical procedure, comprising:
    successively moving the x-ray tube into a plurality of different angular positions;
    switching the flat x-ray detector to sensitive over a time window in each of the different angular positions;
    emitting an x-ray radiation to the flat x-ray detector by the x-ray tube within the time window;
    applying a backlight to the flat x-ray detector within the time window;
    acquiring an x-ray image in each of the different angular positions by the flat x-ray detector within the time window based on the x-ray radiation and the backlight; and
    setting a backlight intensity differently in each of the different angular positions.

2. The method as claimed in claim 1, wherein the backlight is applied over the entire time window.

3. The method as claimed in claim 1, wherein the backlight intensity is a function of a dose of the x-ray radiation.

4. The method as claimed in claim 1, wherein the flat x-ray detector is read area by area after the time window.

5. The method as claimed in claim 4, wherein a further backlight is applied to an area that is already read while reading the flat x-ray detector after the time window to eliminate a residual image structure.

6. The method as claimed in claim 1, wherein the backlight is generated by a plurality of light emitting electrodes.

7. The method as claimed in claim 6, wherein the light emitting electrodes are attached to an opposite side of the flat x-ray detector from a side that receives the x-ray radiation.

8. The method as claimed in claim 1, wherein an angle between a connecting line from the x-ray tube to a point on the flat x-ray detector and a surface normal of the flat x-ray detector is different in each of the different angular positions.

9. The method as claimed in claim 1, wherein the method is used in tomosynthesis.

10. An x-ray device for acquiring a series of x-ray images of an object in a medical procedure, comprising:
    an x-ray tube that is successively moved into a plurality of different angular positions and emits an x-ray radiation to the object within a time window in each of the different angular positions;
    a flat x-ray detector arranged under the object that is switched into sensitive within the time window and acquires an x-ray image of the object;
    a light emitting electrode that applies a backlight to the flat x-ray detector within the time window; and
    a control device that sets a backlight intensity differently in each of the different angular positions.

11. The x-ray device as claimed in claim 10, wherein the flat x-ray detector acquires the x-ray image of the object by detecting the x-ray radiation and the backlight.

12. The x-ray device as claimed in claim 10, wherein the light emitting electrode is attached to an opposite side of the flat x-ray detector from a side that receives the x-ray radiation.

13. The x-ray device as claimed in claim 10, wherein the backlight is applied over the entire time window.

14. The x-ray device as claimed in claim 10, wherein the backlight intensity is a function of a dose of the x-ray radiation.

15. The x-ray device as claimed in claim 10, wherein the flat x-ray detector is read area by area after the time window.

16. The x-ray device as claimed in claim 15, wherein a further backlight is applied to an area that is already read while reading the flat x-ray detector after the time window to eliminate a residual image structure.

17. The x-ray device as claimed in claim 10, wherein the object is a patient.

* * * * *